(12) United States Patent
Pons

(10) Patent No.: US 8,253,279 B2
(45) Date of Patent: Aug. 28, 2012

(54) INDUCTIVE POWER SWITCHING WITH DIGITAL CONTROL FOR ACTIVE IMPLANTABLE DEVICES

(75) Inventor: Pascal Pons, La Buisse (FR)

(73) Assignee: Sorin CRM S.A.S., Clamart (FR)

( * ) Notice: Subject to any disclaimer, the term of this patent is extended or adjusted under 35 U.S.C. 154(b) by 310 days.

(21) Appl. No.: 12/769,483

(22) Filed: Apr. 28, 2010

(65) Prior Publication Data

US 2010/0274301 A1    Oct. 28, 2010

(51) Int. Cl.
*H03K 17/80* (2006.01)

(52) U.S. Cl. ............................................. 307/149; 607/2

(58) Field of Classification Search .................. 307/149, 307/150, 154; 607/2
See application file for complete search history.

(56) References Cited

U.S. PATENT DOCUMENTS

| | | | |
|---|---|---|---|
| 5,649,965 A | 7/1997 | Pons et al. | |
| 5,769,877 A | 6/1998 | Barreras | |
| 7,009,362 B2 * | 3/2006 | Tsukamoto et al. | 320/107 |
| 2004/0082982 A1 | 4/2004 | Gord et al. | |
| 2006/0100674 A1 | 5/2006 | Molin | |
| 2008/0077010 A1 | 3/2008 | Cohen-Solal et al. | |
| 2009/0043244 A1 | 2/2009 | Inan | |

FOREIGN PATENT DOCUMENTS

| | | |
|---|---|---|
| DE | 102006008495 | 9/2007 |
| EP | 0719 570 | 7/1996 |
| EP | 1647303 | 4/2006 |

OTHER PUBLICATIONS

Foreign Search Report (Annexe Au Rapport De Recherche Preliminaire Relatif A La Demande De Brevet Francais No. FR0952775 FA721983), Dec. 8, 2009.

* cited by examiner

*Primary Examiner* — Shawn Riley
(74) *Attorney, Agent, or Firm* — Orrick Herrington & Sutcliffe, LLP

(57) ABSTRACT

An Inductive power switching supply with a digital control for active implantable medical devices is disclosed. A switching power supply (14) receives as input (12) an input voltage ($V_i$) from a battery (10) and delivers as output (16) an output voltage ($V_O$). The switching power supply comprises an inductor having an inductance value (L) and a switching network (S1 ... S5, D1 ... D4), providing, according to a predefined topology, at least two alternative configurations including a charge phase and a discharge phase. The switching network is controlled at the end of the charging and discharging phases and the output voltage is regulated as a function of the input voltage from the nominal voltage. The switching network control does not measure current through the inductor. An analog-to-digital converter (20) is used to deliver a digital value representative of the input voltage ($V_i$). A predictor tool calculates a priori, a duration of the charging phase and a duration of the discharging phase according to a plurality of parameters comprising: the input voltage, the output voltage, the nominal voltage, the inductance value and a predetermined peak current ($I_K$) through the inductor during the charging phase.

14 Claims, 2 Drawing Sheets

INDUCTIVE POWER SWITCHING WITH DIGITAL CONTROL FOR ACTIVE IMPLANTABLE DEVICES

FIELD OF THE INVENTION

The present invention is directed to "active implantable medical devices" (AIMD) as defined by the 20 Jun. 1990 Directive 90/385/EEC of the Council of European Communities, more particularly to such devices that continuously monitor a patient's cardiac rhythm and deliver to the heart, if necessary, electrical stimulation, resynchronization and/or defibrillation pulses, in response to a detected arrhythmia, and even more particularly to power supplies for such devices.

BACKGROUND OF THE INVENTION

A power supply is a particularly critical component of an active implantable medical device, because of the stringent constraints imposed by the dual needs of miniaturization and longevity. The documents U.S. Pat. No. 5,769,877 A, EP 0 719 570 A1, EP 1 647 303 A1, DE 10 2006 008 495 A1, U.S. 2008/0077010 A1, U.S. 2009/0043244 A1 and U.S. 2004/00892982 A1 describe various aspects of a power supply for a medical implantable device.

An active implantable device such as a pacemaker or an implantable defibrillator is typically provided with a battery having a nominal life of about a decade. During its usage, the battery may exhibit notable changes in the voltage between the positive and negative terminals.

Over a long term period, between the time of implantation and the end of the battery life, the average voltage decreases gradually from 3.3 to 2.4 V, a decrease of over 25% from the nominal voltage;

Over a short period, particularly as a result of sudden current peaks, the battery voltage drops due to its own internal resistance.

Concerning more specifically the latter, while the average consumption of a pacemaker is normally about 15 µA, a sudden current peak may occur from time to time, particularly when RF (radio frequency) telemetry functions are activated. This is because the power of the transmitter/receiver requires a greater current of about 5 to 10 mA.

Moreover, in the case of an implantable defibrillator, before delivery of a shock, charging the high voltage output capacitors can create a temporary current peak that can reach from 3 to 4 A. Thus, in extreme cases, the battery voltage may drop to as low as 1.2 V, a voltage drop of more than 50% within a few tens or hundreds microseconds.

These very significant long term and almost instantaneous changes in the voltage require a special power supply circuit for ensuring that the various components of the device deliver a precise and stabilized voltage. The power supply circuit used for this purpose may be of a switching converter type or a SMPS (Switching Mode Power Supply) type.

The principle of SMPS circuits is to operate cyclically, with a primary phase during which an inductor is charged with energy by the voltage delivered by the battery, and a secondary phase during which the inductor is discharged to a user circuit. Buffer capacitors at the input and output of the power supply circuit provide a certain constancy of the output voltage, whose value is regulated by varying the durations of the phases of charging and discharging and/or of the duty cycle of these durations.

Several topologies of switching converters exist, chosen according to the needs. These include so-called buck (with lowering of the voltage), boost (with increasing of the voltage), buck-boost (with lowering or increasing of the voltage, and polarity inversion), and mixed (with lowering or increasing of the voltage without polarity inversion) topologies.

On the other hand, with the same battery it is possible to combine several power supplies dedicated to supply power to the various circuits, said power supplies sharing a same inductor.

The charge and discharge phase control is generally achieved by measuring the current through the inductor. It is powered with a current that is increasing, until it reaches a predetermined value (hereinafter named "peak current"), this value being, for example, based on an error signal measured between the output voltage of the converter and the nominal voltage of the user circuit. When the peak current is reached, the load is interrupted and the inductor is discharged into the user circuit.

The charge/discharge phases can follow each other without interruption, as long as the current delivered during the discharge phase is not equal to zero. This mode of operation is referred to as continuous conduction mode or CCM, and is suitable in terms of performance when the user circuit presents a quasi-permanent relative high load. In contrast, when the discharge current in the inductor is equal to zero, a period of time may elapse between the end of the discharge phase and the start of the charging phase immediately following. This mode is referred to as discontinuous conduction mode or DCM. The DCM method is suitable in terms of performance to a user circuit with a variable load over time, for example, with a relative low load most of the time as in an AIMD.

A first drawback of known switching converters is that they generally operate satisfactorily, with a good yield, as long as the current peak does not exceed a maximum value corresponding to an operation in continuous conduction. However, for a larger current peak, the passage to a discontinuous conduction has the effect of decreasing the yield. To avoid this situation, the switching frequency is reduced to extend the duration of the phases and load the inductor with a higher energy. The counterpart is a significant increase in the peak current at the end of the charge, even when it is necessary to deliver relatively low output voltages. In other words, to increase the current to deliver to the user circuit, it is necessary to increase significantly the permissible peak current, with new constraints on the design of components so that they are able to withstand the higher peak current.

A second drawback of known switching converters is that they are generally poorly adapted to operate "on demand", that is to say an all-or-nothing operation for a circuit that is sporadically used, such as the channels of emission/reception of an RF telemetry circuit or a circuit for delivering a defibrillation shock. In a normal operation, these circuits are not used, thus not fed, and the converter that feeds them is either shut down or put into a low power consumption mode. When they are used, the converter quickly delivers a high current in a short period of time (typically within a fraction of a millisecond). The converter therefore must be able to quickly provide the required voltage in a short period time, which is a very different situation from regulating the power supply in a continuous operation.

A third drawback is that to measure a current through the inductor, it is necessary to place in series with it a resistive element. The first consequence is the introduction of an energy loss, which reduces the overall yield. Moreover, the aging of the component over a long period (typically ten years, the usual lifetime of a cardiac implant) will result in an inaccuracy becoming larger over time, on the measurement of the peak current. The inaccuracy can reach insufficient or excessive levels of the measured peak current by comparison to the predefined value. Thus, for a maximum discharge current of about 10 mA for example, the inductor can be charged with a peak current up to 100 mA, inducing a loss of performance.

A fourth drawback is that the charge and discharge phase sequencing are performed by analog circuits. The imprecision of these analog circuits, including the dispersion of the value of the components and the drift of values during the life of the device, requires taking safety margins when designing the converter. The converter is particularly calculated on the basis of a battery voltage at the end of life, so that its operation is not optimal in early life, thus causing a loss of efficiency, unnecessarily increased consumption and oversized components.

There is, therefore, a need for an improved power supply of the switching converter type being particularly (but not limited to) suitable for active medical implants, overcoming the various constraints outlined above.

OBJECT AND SUMMARY OF THE INVENTION

It is, therefore, an object of the present invention to provide an improved power supply for an active implantable medical device.

The invention proposes to this end an active medical device of a known type comprising: a battery forming a power source of the device and a user circuit to power with the battery with a given nominal voltage, and an inductive switching power supply including an input receiving a continuous unstabilized input voltage produced by the battery, and an output circuit supplying the user circuit with a stabilized output voltage that is different from the input voltage. Preferably, the active medical device is an implantable medical device.

One aspect of the invention is directed towards a switching power supply that comprises an inductor for energy storage, a buffer capacitor and a switching network establishing between the input, the output, the inductor and the capacitor, during successive cycles and in a predefined topology of the switching power supply, with at least two alternative configurations: first, a configuration of energy storage during a charging phase in which the inductance is charged by a current delivered by the battery, with an intensity increasing to a peak, and second, a configuration of energy release during a discharge phase in which the energy stored in the inductor during the charging phase is transferred to the buffer capacitor and from the buffer capacitor to the user circuit. A means for controlling the switching network controls the end of the charging and discharging phases so as to regulate the output voltage depending on the input voltage compared to the given nominal voltage.

In a preferred embodiment of the invention, the means for controlling the switching network comprises essentially no means for measuring the current through the inductor, and comprises an analog-to-digital converter delivering a digital value representative of the input voltage. The means for controlling further comprises a predictor means, with a means of calculation that a priori assesses the duration of the charging and discharging phases according to a plurality of parameters. Preferably, the plurality of parameters comprises: the input voltage, the output voltage, the value of the inductance, and a predetermined value of peak current through the inductor during the charging phase.

In a first embodiment, the predictor means comprises a lookup table memorizing pre-computed values (using a small on-chip memory, e.g., ROM, OTP, Flash, RAM or simple registers) of the duration of the charging and discharging phases against said parameters.

In a second embodiment, the predictor means comprises a means for performing a dynamic computation of the durations of the charging and discharging phases against the aforementioned parameters. Preferably, the means for dynamic calculation of the durations of the charging and discharging phases advantageously comprises a means for determining dynamic durations of the charging and discharging phases, notably with a conditionally activating finite state machine in response to service requests.

The means for controlling may further comprise a selectively activated clock for sequencing and/or for power consumption reduction. For example, the clock is activated only on emission of a service query (or request (REQ)) and deactivated after execution of this query.

Advantageously, the power supply of the present invention provides:

responsive functioning, allowing a sudden current peak to occur in a time interval of a few tens of microseconds;

low intrinsic power consumption with minimal analog components;

high conversion yield with low losses in the conversion circuits;

easy integration on a chip with a minimum of additional external components;

suitability for any topology (e.g., buck, boost, buck-boost or mixed) according to the requirements without redesigning the converter;

ability to work in a wide range of input voltages (e.g. 3.3 to 1.2 V), by dynamically changing the topology;

ability to operate "on demand", the converter being stationary (i.e., inactive or in a very low frequency mode) most of the time, but when placed in service (e.g., RF telemetry, shock defibrillation), responding fast and delivering a high current almost instantly after activation.

BRIEF DESCRIPTION OF THE DRAWINGS

Further features, characteristics, and advantages of the present invention will become apparent to a person of ordinary skill in the art from the following detailed description of preferred embodiments of the present invention, made with reference to the annexed drawings.

DETAILED DESCRIPTION OF THE INVENTION

With reference to the drawings, preferred embodiments of a device of the present invention will now be described. Preliminarily, the invention may particularly be applied to implantable devices such as those of the Reply and Paradym brand device families produced and marketed by Sorin CRM, Clamart, France (formerly known as ELA Medical, Montrouge, France). These devices include programmable microprocessor circuitry to receive, format, and process electrical signals detected by implanted electrodes and deliver pacing pulses to these electrodes. It is possible to download by telemetry software that will be stored in a memory of the implantable devices and executed to implement the functions of the invention that are described herein.

Figure 1:
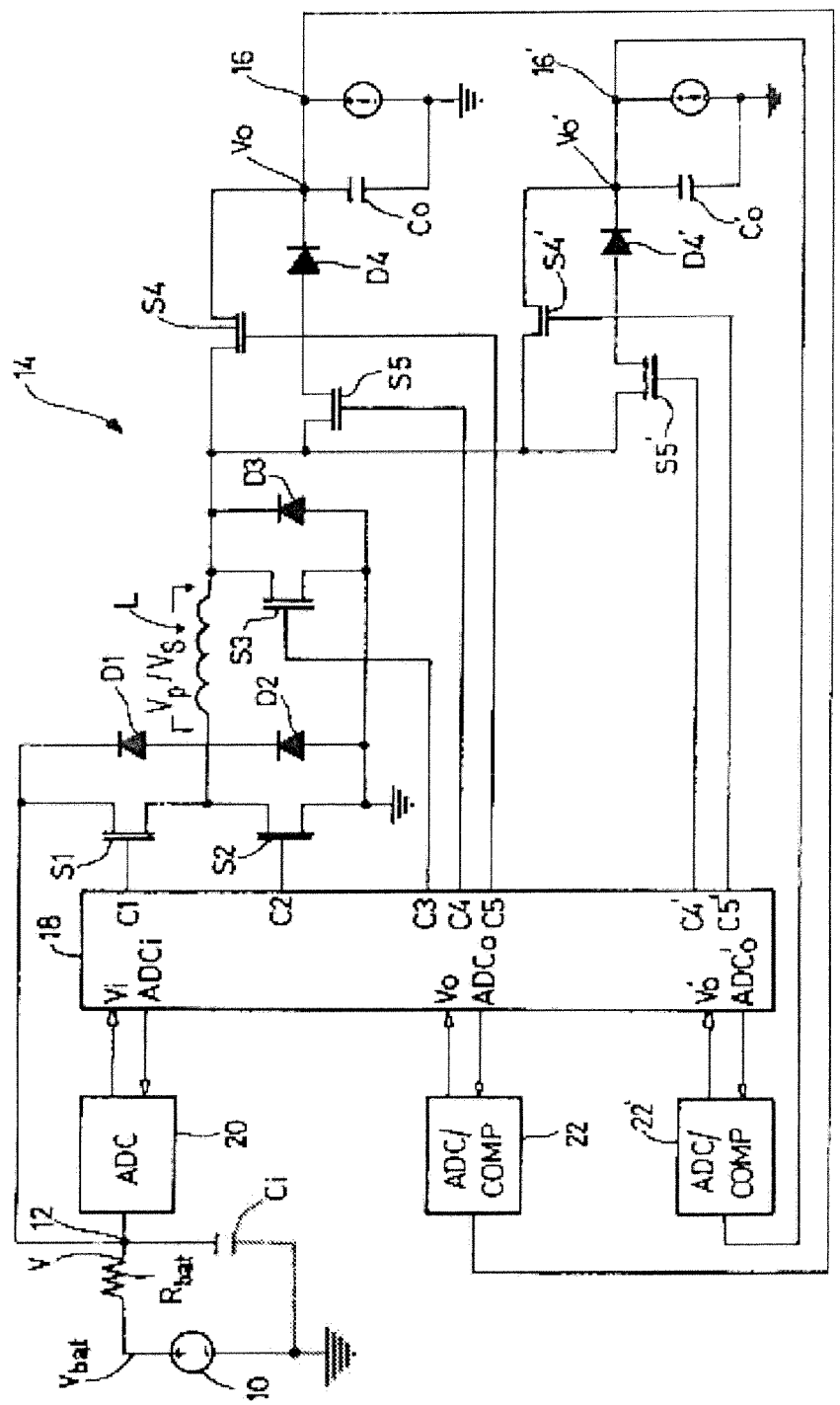
FIG. 1 is a schematic diagram of a switching converter power supply according to an embodiment of the present invention.

Referring to FIG. 1, a power supply for an implantable medical device is shown, with converter 14 having a switching function for the production and regulation of the voltage to power a user circuit. The converter 14 illustrated in FIG. 1 is a "SIMO" (Single Input Multiple Output) type having a single source of continuous voltage input (e.g., battery 10) and multiple outputs with regulated voltages. This configuration provides power for circuits requiring different supply voltages, or circuits that are continuously used (e.g., a circuit of detection and stimulation), while others are only used occasionally in an "on demand" mode (e.g., emitter/receiver telemetry circuit, or circuit for delivering a defibrillation shock), with a large current peak during these occasional uses.

In FIG. 1, a configuration with two conversion stages corresponding to two separate outputs is illustrated, but it should be understood that this example is of course in no way limiting of the scope of the invention. Similarly, other converter topologies may be used as well known to those skilled in the art, which will not be described in detail (e.g., buck to reduce the input voltage, boost to raise it, mixed or buck-boost to increase it as well as to decrease it without reversion of the polarity in one case and with reversion in the other). The selection of the converter topology may be performed without modifying the circuit (except the inversion of the output diode for the buck-boost topology) by a simple change of the switching function at various stages of charging and discharging of an inductor contained in converter 14.

The power supply includes battery 10 of nominal voltage $V_{BAT}$, its Q value measuring the quality of the battery decreasing steadily over the years throughout its lifespan. Given its internal impedance $R_{BAT}$, battery 10 delivers a voltage V, applied to input 12 of converter 14 that is based on the current peak by the user circuits being powered. Converter 14 delivers on its two outputs 16, 16' two regulated output voltages $V_O$, $V'_O$, for the power of the respective user circuits of the device.

Converter 14 is provided with input buffer capacitors $C_I$ and output buffer capacitors $C_O$ and $C'_O$ to absorb the short-term variations of the input and output voltages. The capacity of these capacitors is chosen sufficiently high so that over the duration of a phase of charge or a phase of discharge (see below), the input voltages $V_i$ and the output voltages $V_O$, $V'_O$ are substantially constant.

Converter 14 includes an inductor L alternately submitted to phases of charge and discharge through electronic switches S1, S2, S3, S4, S5 (and S4', S5' for the second stage) and diodes D1 D2, D3 and D4 (and D4' for the second stage). The switches are controlled by respective signals C1, C2, C3, C4, C5 (and C4', C5') generated by digital circuitry 18 whose detailed structure and operation are discussed in detail below with reference to the FIG. 2.

Digital control circuit 18 receives as input digital information representative of the input voltage $V_i$ after it has been digitized by analog to digital converter (ADC) 20 activated on demand by a signal $ADC_i$. ADC converter 20 has a resolution and a response time sufficient to track changes in the input voltage $V_i$ to converter 14 during a short term as well as a long term.

Digital circuitry 18 receives information on the output voltages $V_O$ and $V'_O$ through respective circuits 22 and 22' which may be either analog to digital converters selectively activated by the signals $ADC_O$ and $ADC'_O$ or simple comparators. The latter case may apply in a particular configuration when the output voltage $V_O$ to regulate is close to its nominal value Vref: in other words, when it is sufficient to determine whether the output voltage $V_O$ is or is not within a range $V_{ref} \pm V_A/2$, $V_A$ being the regulation step of the voltage. The use of comparators instead of converters notably simplifies the circuit and reduces power consumption.

An operating cycle of converter 14 is described in an example where converter 14 operates in a mixed topology (thus without polarity inversion) on the first output 16. The operation of the output 16' of the second stage is similar, and thus will not be described.

As it is known, the cyclic operation of a switching converter includes a phase of charge (or primary phase) and a phase of discharge (or secondary phase). Specifically, the cyclic operation includes the following phases:

1) a phase of charge (primary phase): switches S1, S3, S5 are closed, and switches S2, S4 are opened. Inductance L, initially discharged, is mounted between input 12 and the ground, so that the primary voltage $V_P$ at its terminals is equal to $V_i$. Inductor L is charged for a certain time $T_p$ until the current reaches a prescribed value, known as peak current $I_K$. Using a first order approximation in which any phenomenon of resistance in series with inductor L is neglected, and the input and output capacitors $C_I$ and $C_O$ are considered to have a sufficient capacity to consider the voltage $V_i$ and $V_O$ are constant throughout the cycle, $T_P$ is determined by: $T_P \cdot V_P = L \cdot I_K$.

2) a short transition period at the end of the phase of charge: switches S1 and S3 are opened to avoid, just before the closure of switches S2 and S4 (in the next step), the appearance of a low impedance path between the input and the ground. During this transition period, inductor L begins to discharge through diodes D2 and D4 into output capacitor $C_O$.

3) a first phase of discharge, Part I: switches S2, S4, S5 are closed, and switches S1, S3 are opened. Inductor L that is connected between output 16 and the ground—the secondary voltage $V_S$ at its terminals is equal to $V_O$—is discharged during a given period $T_{S1}$, until the current reaches a fixed fraction ρ (e.g., 70%) of the initial peak current $I_K$. As before, using a first order approximation, the period $T_{S1}$ is calculated by: $T_{S1} \cdot V_S = \rho \cdot L I_K$.

4) a secondary phase of discharge, Part II: switch S4 is opened, placing the diode D4 in the path of discharge of inductor L. Inductor L is still connected between output 16 and the ground through D4, but an inversion of the discharge current is avoided. The discharge continues for a period $T_{S2}$ until the current reaches to zero. The upper limit of $T_{S2}$ is given by $T_{S2} \cdot V_S = (1-\rho) L \cdot I_K$.

5) an end of phase discharge: the switch S5 is opened and inductor L is put to the ground via S2 and S3 that are closed in order to avoid any overshoot.

According to one embodiment, the duration of the primary charging phase $T_P$ and the duration of the secondary discharging phase $T_S$ ($T_S = T_{S1} + T_{S2}$) are calculated a priori based on measured input and output information and the peak current to reach. This approach is contradictory to the traditional approach that measures the current through the inductor, monitors changes throughout the charge cycle, and interrupts the load when the current reaches the preset value of current peak, the durations of the charging and discharging phases being subsequently settled as a result of controlling the charge and discharge.

$T_P$ and $T_S$ are obtained by:

$$T_P = -\frac{L}{R_P} \log\left(1 - \frac{R_P I_K}{V_P}\right),$$

and

-continued $$T_S = +\frac{L}{R_S}\log\left(1 + \frac{R_S I_K}{V_S}\right),$$

where $R_P$ and $R_S$ are the values of the resistive components in series with inductor L during the respective phases of charge and discharge.

These relations are written as a first order approximation in simplified forms:

$$T_P = \frac{LI_K}{V_P} \text{ and } T_S = \frac{LI_K}{V_S},$$

where $V_P$ and $V_S$ are chosen for the converter topology selected, according to the following table:

|  | Buck | Boost | Mixed | Buck-Boost |
|---|---|---|---|---|
| $V_P$ | $V_I - V_O$ | $V_I$ | $V_I$ | $V_I$ |
| $V_S$ | $V_O$ | $V_O - V_I$ | $V_O$ | $-V_O$ |

Note that in a buck-boost topology, the output voltage $V_O$ is negative.

As can be seen, the durations of primary and secondary phases are a function of the input and output voltages, as well as inductor L and the predetermined peak current $I_K$ that depend on the converter topology.

The input voltage $V_i$ and the output voltage $V_O$ vary over time. However, as noted above, if converter 14 operates when the output voltage $V_O$ is close to its nominal value $V_{ref}$ (that is to say $V_o$ will always be in the range of $V_{ref} \pm V_A/2$), the output voltage $V_O$ may be considered as constant over time. It is therefore possible to proceed in a simple way by calculating in advance the values of primary and secondary time durations for each value of the input voltage, and saving those values in a correspondence table (e.g., a table for each topology), or in a simple register if a simplified topology such as buck-mode or mixed with a constant value $T_S$ is used.

According to another embodiment, durations $T_P$ and $T_S$ are calculated in real time by appropriate digital control circuits as a function of the instantaneous values of the input voltage $V_I$ and the output voltage $V_O$.

Figure 2:
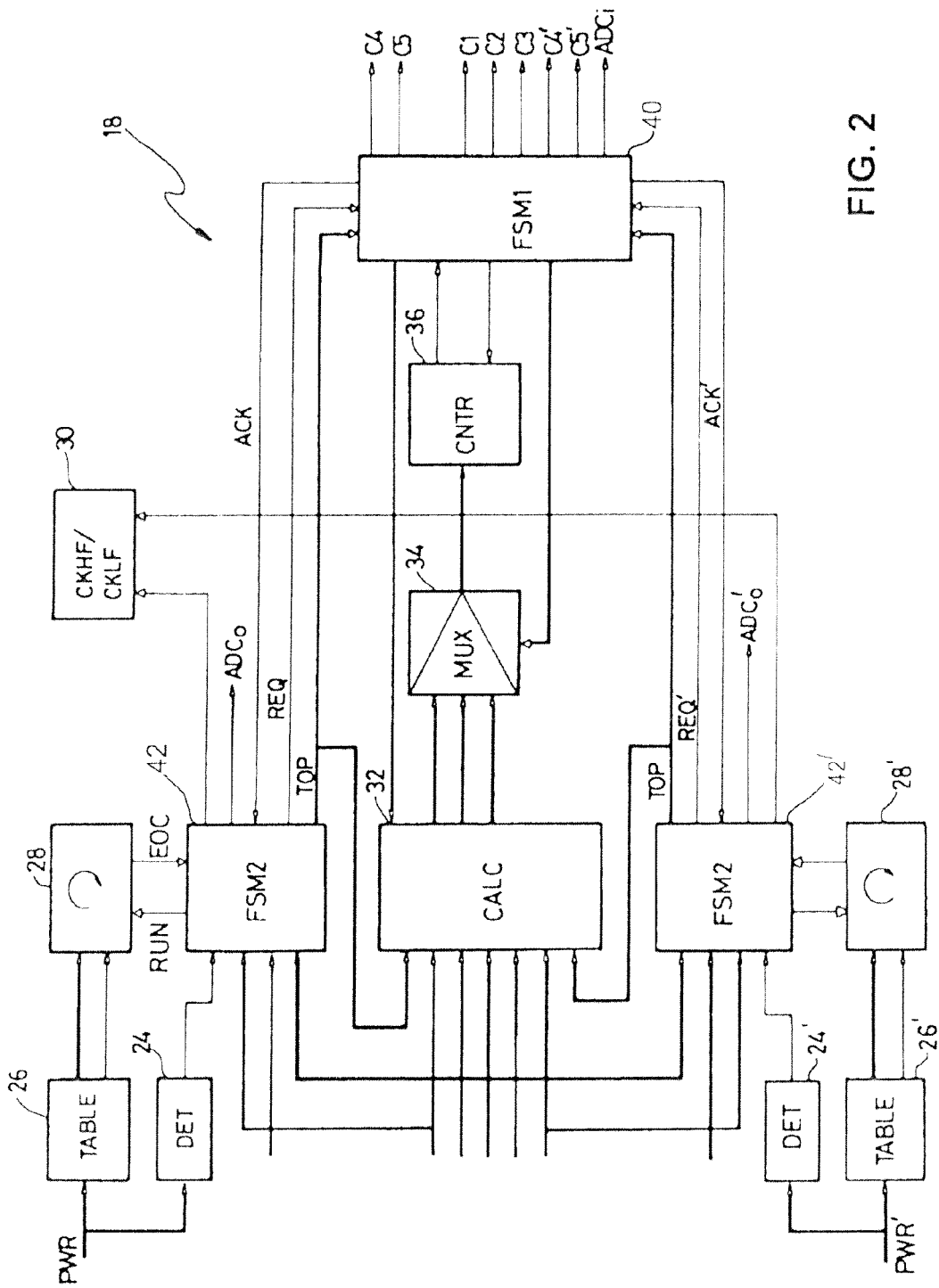
FIG. 2 is a schematic diagram of the digital controller of the converter of FIG. 1.

With reference to FIG. 2, a preferred embodiment of the digital control circuit 18 is described. This circuit has three finite state machines (FSMs) referenced as 20, 22 and 22'.

Controller 40 is a switch controller, which controls switches S1, S2 . . . S5 described above in reference to FIG. 1. Controllers 42 and 42' are monitors that monitor the output voltages $V_O$ and $V'_O$ on the respective outputs 16 and 16'. Controller 42' controls the second stage of converter 14 (output 16'), and the other circuits of the second stage. Its operations are identical in structure and function to controller 42 of the first stage (output 16), and thus are not described in detail.

When controller 22 detects that the output voltage $V_O$ has fallen below its nominal value, it delivers to switch controller 40 a service query (REQ). If controller 40 is not yet active due to a request from the other controller 42', it initiates a cycle of charge/discharge in response to the query REQ. Once this cycle is completed, controller 40 sends to controller 22 an acknowledgment (ACK) and waits for another query REQ. Controller 42, meanwhile, continues to monitor the output voltage $V_O$.

The circuits associated with controllers 40 and 42 reduce the size of controlling circuit 18, thus reducing the power consumption of switching converter 14. This is particularly advantageous for implanted medical devices.

A first step to save energy is to optimize the use of the system clock. The system clock is a high frequency clock CKHF, in the order of Megahertz or higher with a period $T_C$ consistent with the algorithms for calculating the periods $T_P$ and $T_S$. Insofar as the power consumption of a digital system is roughly proportional to its clock speed, the system clock is stopped when not in use, for example, when the output voltages are above their nominal values. The system starts monitoring the output voltages when these voltages fall below these thresholds. The clock CKHF is activated when one of the elements of the regulator, typically controller 42 or 42', delivers a service query REQ, and is deactivated once the query REQ has been processed by switch controller 40. This implies that controllers 42 and 42' and the circuits directly related to them operate without the system clock CKHF.

A first possibility is that controllers 42, and 42' may be implemented in analog circuits, such as comparators. Comparators are simple, safe, and easier to implement, but continuously consume power of at least a few microamperes.

Another preferred embodiment is to minimize analog elements and to use a digital circuit sequenced by a second clock, hereafter CKLF. The second clock is permanently active, but its frequency is much lower than that of clock CKHF, for example, a frequency of 32 kHz. The duration between two successive cycles of charge/discharge of converter 14 is considered long compared to the period of the low frequency clock CKLF. The output voltage is monitored while minimizing power consumption required for the monitoring function.

According to one embodiment, the output voltage is controlled by a digital controller with a timer that disables the high frequency clock CKHF for a long period, for example, one millisecond. The digital controller may be used when the current values and the moments of current needs are predictable, for example, it is known in advance when a defibrillation shock will be delivered, or that a telemetry function will be activated. Given the capacity of the output capacitor $C_O$, the output voltage $V_O$ is controlled not to fall by more than a predetermined value, for example, no more than 5 mV, converter 14 immediately compensates for the voltage drop in the next cycle of charge/discharge.

Referring to FIG. 2, control circuit 18 receives as input a digital bus PWR representative of the current consumption of the device. The value of PWR is stored in a register of detector 24. Detector 24 detects a change of PWR in order to wake up the finite state machine of controller 42 from a sleep state.

Table 26 stores, for each level of consumption PWR, information such as:

interval between two levels of the output voltage $V_O$;

peak current $I_K$ as a function of the input current (an increased peak current increases the period between two successive detections, and vice versa);

selection of the clock to be used (for high levels of consumption, the fast clock may be necessary to increase the responsiveness of the converter).

Timer 28 determines the intervals during which changes in the output voltage $V_O$ are detected. Timer 28 is activated by controller 42 for measuring the output voltage $V_O$ when it goes to a sleep mode. Controller 42 in sleep receives later a wake-up signal EOC when timer 28 finished its counting.

According to one embodiment, controller 42 operates as a finite state machine FSM as follows.

Firstly, controller 42 produces a signal $ADC_O$ of activation of converter 14 measuring the output voltage $V_O$. Converter 14 may be, as indicated above, a simple comparator. If the output voltage $V_O$ exceeds the nominal value $V_{ref}$, controller 42 activates timer 28 (via RUN signal) and enters into a sleep mode according to the clock used by timer 28. If timer 28 works with the system clock CKHF, controller 42 goes into a wait loop, but continues to activate clock manager 30 so that it maintains the high frequency system clock CKHF active. Otherwise, controller 42 informs clock manager 30 of the possibility to disable the system clock CKHF provided that the other controller 42' does not grant an opposite query. Controller 42 may choose the switching topology, and this information TOP is transmitted to both controller 40 and digital circuit 32 to determine the durations of phases of charge and discharge.

According to one embodiment, the control circuit of controller 40 is made by a finite state machine FSM. The FSM works in a loop, waiting for a service request REQ from one of controllers 42 and 42'. Upon receipt of a service request, the input is measured, and ADC converter 20 is activated by an activation signal $ADC_i$. The measured value is applied to digital circuit 32 which determines the duration of $T_P$ and $T_S$ (more precisely, $T_P$, $T_{S1}$ and $T_{S2}$) as a multiple of the period $T_C$ of the clock CKHF. The values calculated by the digital circuit 32 are used, via multiplexer 34 and counter 36 to implement the various switches described above, according to the calculated durations and the selected converter topology.

As mentioned above, digital circuit 32 determines the various durations $T_P$, $T_{S1}$ and $T_{S2}$ either from a table of correspondence, or by directly calculating these values in real time. The parameters to be taken into account in determining $T_P$, $T_{S1}$ and $T_{S2}$ include, but are not limited to:
the input voltage $V_i$;
the output voltage $V_O$;
the nominal voltage $V_{ref}$;
the converter topology;
the inductance value of inductor L;
the peak current $I_K$ (with possibly different values depending on the converter topology);
the percentage ρ defining the beginning of the second part of the $T_{S2}$ discharge phase where a diode is inserted in the discharge path to prevent reverse current;
the resistance $R_L$ of the inductance (if more detailed calculation models are used).

Some of these parameters are obtained by the result of an analog to digital conversion ($V_I$, $V_o$), others are determined by another block (e.g., choice of the converter topology), and others are stored in memory or in a register set (e.g., $V_{ref}$, $I_K$, L, R, and ρ).

In a preferred embodiment, a correspondence table is used to calculate the periods $T_P$, $T_{S1}$ and $T_{S2}$ in advance and store them in a table or in registers. Insofar as the computation time is not an obstacle, this technique allows especially to use complex mathematical relationships, taking into account a large number of parameters and/or nonlinear functions.

In another embodiment, the periods $T_P$, $T_{S1}$ and $T_{S2}$ are calculated in real time with simplified models to calculate the various parameters. This approach has an advantage that the parameters of the calculation can be changed on the fly, for example, to adjust the peak current $I_K$ depending on the selected topology or the level of power consumption. Similarly, the nominal voltage $V_{ref}$ and the value of the inductor can be adapted over time to reflect system changes such as aging or other conditions that require to adjust the nominal voltage.

The primary phase of load TP is calculated by:

$$T_P = \frac{LI_K}{V_P}$$

which is rewritten after discretization in the form:

$$t_P = \frac{LI_{KO}}{T_C V_A} \cdot \frac{k}{v_P},$$

with $T_P = T_C t_P$, $I_K = I_{KO} k$, $V_P = V_A v_P$, $t_P$, k and $v_P$, being integers, $I_{KO}$ being a programmable minimum value of peak current, and $v_P$ being an integer which is a parameter determined by the analog to digital voltage conversion.

Similarly, the discharge phase $T_S$ is calculated with $v_S$ instead of $v_P$. The durations of both phases $T_{S1}$ and $T_{S2}$ are given by $T_{S1} = \rho \cdot T_S$ and $T_{S2} = T_S - T_{S1}$. A fixed value ρ may be chosen for example, ρ=0.75, to simplify the circuit.

It should be understood that, since $T_P$, $T_{S1}$ and $T_{S2}$ are needed successively, but not simultaneously, their calculation does not need to be done in parallel and can be serialized and thus executed by the same circuit. However, if one uses a lookup table, the table provides each of those periods respectively.

One skilled in the art will appreciate that the present invention can be practiced by embodiments other than those described herein, which are provided for purposes of illustration and not of limitation.

The invention claimed is:
1. An active medical device, comprising:
a battery (10) providing an input voltage ($V_i$);
a user circuit powered at a nominal voltage (Vref);
a switching power supply (14) comprising:
(1) an input (12) receiving the input voltage ($V_i$);
(2) an output (16) supplying the user circuit with an output voltage ($V_O$);
(3) an inductor having an inductance value (L);
(4) a buffer capacitor ($C_O$);
(5) a switching network (S1 ... S5, D1 ... D4), providing between the input, the output, the inductor and the buffer capacitor during successive cycles and according to a predefined topology of the switching power supply, at least two alternative configurations, including:
(a) a charging phase configuration of energy storage, wherein the inductor is charged by a current delivered by the battery, the current having an increasing intensity up to a peak current ($I_K$), and
(b) a discharge phase configuration of energy release, wherein the energy accumulated in the inductor during the charging phase is transferred to the buffer capacitor and from the buffer capacitor to the user circuit, and
(6) means (18, 20, 22) for controlling the switching network at the end of the charging phase and the discharging phase so as to regulate the output voltage as a function of the input voltage from the nominal voltage, wherein said means for controlling the switching network comprises:
(a) no means for measuring the current through the inductor;
(b) an analog to digital converter (20) delivering a digital value representative of the input voltage ($V_I$); and

(c) a predictor means for calculating a priori a duration of the charging phase and a duration of the discharging phase, each duration being calculated according to a plurality of parameters comprising: the input voltage ($V_I$), the output voltage ($V_O$), the nominal voltage ($V_{ref}$), the inductance value (L), and the peak current ($I_K$).

2. The device of claim 1, wherein the predictor means further comprises a lookup table storing precomputed values of the durations of the charging phase and the discharging phase according to said plurality of parameters.

3. The device of claim 1, wherein the predictor means comprises means for dynamically calculating said durations of the charging phase and the discharging phase according to said plurality of parameters.

4. The device of claim 3, wherein the means for dynamically calculating the durations of the charging phase and the discharging phase comprises a finite state machine conditionally activated by a service query REQ from one of the means (18, 20, 22) for controlling the switching network.

5. The device of claim 4, wherein the means for controlling the switching network further comprises a timer, said timer comprising means for turning on in response to the service query, and off after execution of said service query.

6. The device of claim 5, wherein the means for controlling the switching network enters into a sleep mode when the output voltage exceeds the nominal voltage, and the timer counts a predetermined number of counts.

7. The device of claim 6, wherein the means for controlling the switching network enters into a wake-up mode either when the timer expires after counting the predetermined number of counts or the service query is received during the sleep mode.

8. A switching power supply (14) providing power to a user circuit at a nominal voltage (Vref), the switching power supply comprising:
  (1) an input (12) receiving an input voltage ($V_i$) from a battery (10);
  (2) an output (16) supplying the user circuit with an output voltage ($V_O$);
  (3) an inductor having an inductance value (L);
  (4) a buffer capacitor ($C_O$);
  (5) a switching network (S1...S5, D1...D4), establishing between the input, the output, the inductor and the buffer capacitor during successive cycles and according to a predefined topology of the switching power supply, at least two alternative configurations, including:
    (a) a charging phase configuration of energy storage, wherein the inductor is charged by a current delivered by the battery, the current having an increasing intensity up to a peak current ($I_K$), and
    (b) a discharge phase configuration of energy release, wherein the energy accumulated in the inductor during the charging phase is transferred to the buffer capacitor and from the buffer capacitor to the user circuit, and
  (6) means (18, 20, 22) for controlling the switching network at the end of the charging phase and the discharging phase so as to regulate the output voltage as a function of the input voltage from the nominal voltage, wherein said means for controlling the switching network comprises:
    (a) no means for measuring the current through the inductor;
    (b) an analog to digital converter (20) delivering a digital value representative of the input voltage ($V_I$); and
    (c) a predictor means for calculating a priori a duration of the charging phase and a duration of the discharging phase, each duration being calculated according to a plurality of parameters comprising: the input voltage ($V_I$), the output voltage ($V_O$), the nominal voltage ($V_{ref}$), the inductance value (L), and the peak current ($I_K$).

9. The switching power supply of claim 8, wherein the predictor means further comprises a lookup table storing precomputed values of the durations of the charging phase and the discharging phase according to said plurality of parameters.

10. The switching power supply of claim 8, wherein the predictor means comprises means for dynamically calculating said durations of the charging phase and the discharging phase according to said plurality of parameters.

11. The switching power supply of claim 10, wherein the means for dynamically determining calculating the durations of the charging phase and the discharging phase include comprises a finite state machine conditionally activated by a service query from one of the means (18, 20, 22) for controlling the switching network.

12. The switching power supply of claim 11, wherein the control means for controlling the switching network further comprises a timer, said timer comprising means for turning on in response to a the service query, and off after execution of said query.

13. The switching power supply of claim 12, wherein the means for controlling the switching network enters into a sleep mode when the output voltage exceeds the nominal voltage, and the timer counts a predetermined number of counts.

14. The switching power supply of claim 13, wherein the means for controlling the switching network enters into a wake-up mode either when the timer expires after counting the predetermined number of counts or the service query is received during the sleep mode.

* * * * *